United States Patent [19]

Duey, Jr.

[11] Patent Number: 4,496,488

[45] Date of Patent: Jan. 29, 1985

[54] COPPER AND MANGANESE REMOVAL FROM $C_6$-$C_9$ SATURATED ALIPHATIC MONOCARBOXYLIC ACIDS

[75] Inventor: Clarence J. Duey, Jr., Bay City, Tex.

[73] Assignee: Celanese Corporation, New York, N.Y.

[21] Appl. No.: 480,568

[22] Filed: Mar. 30, 1983

[51] Int. Cl.$^3$ .............................................. C11C 1/00
[52] U.S. Cl. ..................................... 260/413; 502/27; 260/419; 423/42; 423/50
[58] Field of Search ............... 252/413; 260/429 R, 260/438.1, 413 R, 419

[56] References Cited

U.S. PATENT DOCUMENTS

| | | | |
|---|---|---|---|
| 3,251,646 | 5/1966 | Alon et al. | 260/439 R X |
| 3,846,460 | 11/1974 | Fite | 260/439 R X |
| 4,246,185 | 1/1981 | Wood | 260/413 R |
| 4,257,913 | 3/1981 | Fischer | 260/429 R |
| 4,289,708 | 9/1981 | Scott et al. | 260/413 R |

*Primary Examiner*—Helen M. S. Sneed
*Attorney, Agent, or Firm*—L. I. Grim; M. Turken

[57] ABSTRACT

A process is described for removing copper and manganese ions from a saturated aliphatic monocarboxylic acid containing from 6 to 9 carbon atoms by extracting the metal ions into an aqueous layer in the presence of an extractant acid, the hydrogen of which can be replaced by both metal ions. The metal ion-containing aqueous layer may then be separated from the monocarboxylic acid-containing organic layer, with the latter layer having a substantially reduced content of copper and manganese ions.

4 Claims, No Drawings

COPPER AND MANGANESE REMOVAL FROM C$_6$–C$_9$ SATURATED ALIPHATIC MONOCARBOXYLIC ACIDS

This invention relates to a process for removing copper and manganese metal ions from a saturated aliphatic monocarboxylic acid containing 6 to 9 carbon atoms. More specifically, the catalyst metal ions copper and manganese, are extracted from a C$_6$–C$_9$ saturated aliphatic monocarboxylic acid in the presence of water and an extractant acid whose hydrogen can be replaced by the cupric and manganous ions. Two layers will form, an aqueous layer containing the acid with the metal ions and an organic layer containing the monocarboyxlic acid. Separating the layers, the organic monocarboxylic acid layer recovered will be substantially free of the magnanous and cupric ions which are present in the aqueous layer. Further purification by distillation of the recovered monocarboxylic acid can be achieved without any tendency for the cupric ions to plate out on the distillation equipment.

BACKGROUND OF THE INVENTION

When oxidizing organic saturated aliphatic aldehydes containing 5 to 9 carbon atoms to the corresponding monocarboxylic acids, an important objective is to obtain sufficiently high yields and product efficiencies at high conversion levels in a single pass, to avoid the necessity to recycle significant amounts of unreacted starting materials. Catalysts comprising copper and manganese facilitate this objective, since they result in the production of larger amounts of acid per pass than do manganese catalysts alone. However, a disadvantage which may result from the use of copper-manganese catalysts in aldehyde oxidation processes, particularly ones in which the reaction product must be distilled to recover the desired product, is the plating out of copper in the distillation apparatus. Plating out can lead to undesirable mechanical problems including erosion of reboilers and pump impellers, and rapid pump seal failures.

Copending U.S. application Ser. No. 345,890 filed Feb. 4, 1982, assigned to Celanese Corporation claims a process of the type described utilizing a copper-manganese catalyst. This process provides relatively high carbon efficiencies of aldehyde to acid at high aldehyde conversions. A single stage or two stage liquid phase reactor system generally gives sufficiently high aldehyde conversions so that recycle of unreacted aldehyde is, in most cases, unnecessary. However, when the reaction mixture is distilled to recover the acid, copper tends to precipitate and plate out on the distillation apparatus unless something is done to prevent it.

One means of overcoming this problem is to add oxalic acid to precipitate copper and manganese from the reaction mixture as their oxalates, prior to the distillation step. This process is described in U.S. Pat. No. 4,289,708, issued Sept. 15, 1981 to Scott et al and assigned to Celanese Corporation. Copper and manganese can also be separated from the reaction mixture by precipitating them, again as their oxalates, by adding an aqueous oxalic acid solution. In this case, the manganese and copper oxalates precipitate into the aqueous phase, which can be readily separated from the organic acid product by decantation. The acid can then be further purified by distillation. However, aqueous oxalic acid cannot be used satisfactorily to treat mixtures containing valeric acid due to this acid's high solubility in water. This process is described in U.S. Pat. No. 4,246,185, issued Jan. 20, 1980 to Wood, Jr. and assigned to Celanese Corporation.

It is the purpose of this invention to provide another technique for removing manganese and copper from C$_6$–C$_9$ saturated aliphatic monocarboxylic acids and avoid the use of oxalic acid and the oxalate precipitates to remove the catalyst metal ions from the acid products.

THE INVENTION

It has been discovered that cupric and manganous ions can be extracted from aliphatic saturated monocarboxylic acids containing 6 to 9 carbon atoms by the addition of a dilute aqueous extractant acid whose hydrogen can be replaced by the cupric and manganous metal ions present in the monocarboxylic acids. The C$_6$–C$_9$ aliphatic saturated monocarboxylic acids are water-immiscible and will form an organic layer in the presence of water. The dilute aqueous extractant acid in this case will form an aqueous layer containing the metal ions which have been extracted from monocarboxylic acids. The monocarboxylic acid can be recovered, with a substantially reduced content of cupric and manganous metal ions and readily purified by normal distillation procedures thus minimizing the problem of cupric ions plating out on the distillation equipment. The aqueous extractant acid layer containing the metal ions recovered can be removed from the system and disposed of or, if desired, the metal ions can be recovered and reused in the form of cupric and manganous oxidation catalysts.

Copending U.S. application Ser. No. 466,447 filed Feb. 15, 1983, assigned to the same assignee as the instant case, describes a process for removing copper and manganese metal ions from an organic phase comprising a saturated aliphatic monocarboxylic acid containing 5 to 9 carbon atoms by extraction with aqueous formic acid, only. This is accomplished by forming cupric and manganous formates which are soluble in the aqueous formic acid. The resulting solution forms an aqueous layer which readily separates from the organic layer containing the monocarboxylic acids substantially free of the manganous and cupric metal ions. Another copending application, U.S. Ser. No. 466,448 filed Feb. 15, 1983, assigned to the same assignee as the instant case, describes a technique for recovering the cupric and manganous formates from the aqueous layer by heating the formates to high temperatures in the presence of added saturated aliphatic monocarboxylic acids having 5 to 9 carbon atoms. The formates react with the monocarboxylic acids to form the corresponding cupric and manganous alkanoates. The alkanoates are recovered by distilling off the water in the presence of an oxygen-containing gas to prevent the copper from plating out. The cupric and manganous alkanoates recovered are satisfactory oxidation catalysts and can be reused in the oxidation of C$_5$–C$_9$ saturated aliphatic aldehydes to the corresponding saturated aliphatic monocarboxylic acids.

In this invention, the organic monocarboxylic acids containing manganous and cupric metal ions, which are treated by means of this process include n-hexanoic acid oxidized from n-hexanal; n-heptanoic acid oxidized from n-heptanal; n-octanoic acid oxidized from n-octanal; n-nonanoic acid oxidized from n-nonanal and isomers of these acids.

The manganese and copper metal ions in the organic monocarboxylic acids are soluble and usually in the form of cupric and manganous compounds. The manganese must be kept in a +2 oxidation state to be soluble in the acid water layer. This can be accomplished by a reduction of manganese by the unreacted aldehyde under a blanket of nitrogen wherein manganese will, in the presence of the reaction aldehyde reaction product, reduce from a +3 oxidation state to a +2 oxidation state. If manganese is in a +3 oxidation state the effectiveness of the process of this invention will be reduced.

It is desired to operate the extraction at ambient temperatures to save energy requirements although higher temperatures can be used with the disadvantage that as the temperatures increase, the organic monocarboxylic acid can become more soluble in the aqueous phase and additional acids can be lost in the recovery system.

During and after the extraction of cupric and manganous ions from the organic phase in the phase, two distinct layers readily form, an organic phase containing monocarboxylic acid and an aqueous phase. The organic layer, substantially free of the copper and manganese metal ions can be separated from the aqueous layer containing the copper and manganese metal ions. From the organic layer, the recovered organic monocarboxylic acid can be further purified by distillation. The manganese and copper metal ions in the aqueous layer can be disposed of or the metal ions can be recovered as oxidation catalysts for use in the $C_6$-$C_9$ aldehyde oxidation reaction to the respective $C_6$-$C_9$ saturated aliphatic organic acids.

The aqueous extractions of cupric and manganese ions from the aliphatic saturated $C_6$-$C_9$ monocarboxylic acids used in this invention can be conducted using a batch technique, a cross current batch extractor, a continuous counter current extractor or the like, whichever is convenient.

The acids which can be used as an extractant acid in the process of this invention include the mineral acids such as sulfuric, hydrochloric, nitric, phosphoric and the like, and formic acid. Acetic acid is weak and would not effectively extract the cupric and manganese metal ions. The use of sulfuric acid will effectively extract the metal ions from the monocarboxylic acids but a small amount of sulfuric acid will remain in the monocarboxylic acids which is not desirable in the production of end uses of the acid product. Hydrochloric acid will also effectively remove the metal ions from the monocarboxylic acid; however, hydrochloric acid and sulfuric acid create extensive corrosion problems in the metal equipment. The preferred acids include nitric acid, phosphoric acid and formic acid. All these acids are compatible and a minimum amount of corrosion exists with these catalysts in the process of this invention.

The amount of acids present in the process of this invention is sufficient to provide at least an equivalent amount of acid per equivalent of the total cupric and manganous metal ions present. In some instances, the amount of acid will be present from about two to about ten equivalents or higher per equivalent of the total metal ions present.

The water in the process of this invention must be present in sufficient amounts to saturate the monocarboxylic acids and provide for an aqueous layer wherein the cupric and manganous metal ions are collected. If sufficient water is not present, the extraction process will flood and not permit an organic acid and aqueous layer to form.

The present invention is illustrated by the following examples:

EXAMPLES 1–7

A continuous counter current extractor was used to remove cupric and manganese ions from heptanoic acid. A one inch internal diameter glass extractor was packed with nichrome helices ($1 \times 2 \times 2$ mm). In these examples, the extractor used either one or two five foot sections of packing.

Aqueous acid was fed into the upper section or midpoint section of the extractor and heptanoic acid containing manganese and cupric ions was fed in the lower section of the extractor. The metal ion-containing heptanoic acid was fed continously. The flow of the water effluent residue (heavy aqueous phase) takeoff was manually adjusted to maintain the oil-water interface at the correct level. The light organic phase comprising mainly heptanoic acid overflowed into a receiving vessel. A pulsation pump was used on all runs to reduce flooding and achieve better extraction. The pump was connected to the column residue. The pulse frequency was 31 pulses per minute and the volume was about 3 milliliters per pulse. The extractor temperature was 25° C. for all runs. In examples 3 to 7, the metal ion-containing heptanoic acid feed containing unreacted aldehyde was treated under a blanket of nitrogen at a temperature of 66° C. for 15 minutes minutes to reduce the manganese ions to the manganous (+2) state. This was not done in example 2. The feeds and amounts of copper and manganese remaining in the heptanoic acid and in the aqueous phase are shown in Table I.

TABLE I

Continuous Extraction of Copper and Manganese from Heptanoic Acid

| Example | Extraction Dimensions | Upper Water Feed | Mid-Point Feed | Lower Heptanoic Acid Feed | Upper Organic Phase Product Cu PPM | Mn PPM | Water Wt. % | Lower Aqueous Phase Product Cu PPM | Mn PPM | $C_7$ Acid Wt. % |
|---|---|---|---|---|---|---|---|---|---|---|
| 1 | 5 ft × 1" | 0.95 ml/min 0.4 N HNO$_3$ | — | 17 ml/min[1] | 2.2 | 0.7 | — | — | — | — |
| 2 | 5 ft × 1" | 1.74 ml/min 0.4 N HNO$_3$ | — | 17 ml/min[2] | 2.3 | 400 | — | — | — | — |
| 3 | 5 ft × 1" | 1.74 ml/min 0.4 N HNO$_3$ | — | 17 ml/min[3] | 0.6 | 1.3 | — | — | — | 0.33 |
| 4 | 10 ft × 1" | 1.08 ml/min 0.4 N HNO$_3$ | — | 16.4 ml/min[3] | 0.2 | <0.1 | 3.97 | — | — | — |
| 5 | 10 ft × 1" | 1.39 ml/min 0.3 N HNO$_3$ | — | 11.9 ml/min[3] | <0.1 | <0.1 | 3.88 | 3900 | 2790 | 0.29 |
| 6 | 10 ft × 1" | 1.39 ml/min 0.3 N HNO$_3$ | — | 11.9 ml/min[3] | <0.1 | <0.1 | 3.24 | 1440 | 890 | 0.27 |
| 7 | 10 ft × 1" | 0.85 ml/min | 0.55 ml/min | 11.9 ml/min[3] | <0.1 | <0.1 | 4.16 | 3540 | 2980 | 0.27 |

TABLE I-continued
Continuous Extraction of Copper and Manganese from Heptanoic Acid

| Example | Extraction Dimensions | Upper Water Feed | Mid-Point Feed | Lower Heptanoic Acid Feed | Upper Organic Phase Product | | | Lower Aqueous Phase Product | | |
|---|---|---|---|---|---|---|---|---|---|---|
| | | | | | Cu PPM | Mn PPM | Water Wt. % | Cu PPM | Mn PPM | C7 Acid Wt. % |
| | | water | 0.8 N HNO3 | | | | | | | |

(1) heptanoic acid containing 300 PPM each Cu (Cupric) and Mn (Manganous) from acetate salts
(2) heptanoic acid oxidized from heptanal containing 600 PPM each Cu and Mn wherein Mn is percent as MnIII
(3) heptanoic acid oxidized from heptanal containing 300 PPM each Cu and Mn In example 1, the amount of cupric ions and manganous ions in the upper phase at 2.2 parts per million can be reduced by increasing the amount of nitric acid into the extractor as illustrated in example 3. Example 2 illustrates the difficulty of removing the manganese when it is in the manganese III state and not the manganous II state. Examples 4 through 6 illustrate the effectiveness of removing cupric and manganous ions from the heptanoic acid. Example 7 demonstrates a slight modification of examples 1 through 6 by adding water at the upper section of the extractor and nitric acid at the mid-point of the extractor. The separation of the cupric and manganous ions from the heptanoic acid is effective.

EXAMPLE 8

A five stage batch cross current extraction was conducted to separate cupric (Cu) and manganous (Mn) ions from heptanoic acid using aqueous nitric acid as the extractant. Heptanoic acid containing 600 parts per million cupric ions and 600 parts per million manganous ions, was fed to the first stage. Ten weight percent of 0.4N nitric acid was added to the first stage and the Cu and Mn determination made of the aqueous phase (water-acid effluent) and the heptanoic acidcontaining organic phase. The heptanoic acid recovered was then sent to the second stage and again a ten weight percent 0.4N nitric acid was added to the heptanoic acid. The metal content was determined in the recovered heptanoic acid and the aqueous phase (water-acid effluent). This procedure was repeated through five stages and the results are shown in Table II.

TABLE II
Cross Current Extraction of Heptanoic Acid Containing Cupric and Manganous Ions

```
                          ↑  Heptanoic Acid
                          |    <0.2 PPM Cu (Cupric)
                          |    0.8 PPM Mn (Manganous)
                          |
                          |           Water-Acid Effluent
   10 wt. %  ─────→ Stage 5 ─────→ 0.6 PPM Cu
   0.4 N HNO3                         1.0 PPM Mn ↑  Heptanoic Acid
                          |    <0.2 PPM Cu
                          |    1.0 PPM Mn
                          |
                          |           Water-Acid Effluent
   10 wt. %  ─────→ Stage 4 ─────→ 5.7 PPM Cu
   0.4 N HNO3                         4.9 PPM Mn ↑  Heptanoic Acid
                          |    0.44 PPM Cu
                          |    1.0  PPM Mn
                          |
                          |           Water-Acid Effluent
   10 wt. %  ─────→ Stage 3 ─────→ 47 PPM Cu
   0.4 N HNO3                         38 PPM Mn ↑  Heptanoic Acid
                          |    0.98 PPM Cu
                          |    1.5  PPM Mn
                          |
                          |           Water-Acid Effluent
   10 wt. %  ─────→ Stage 2 ─────→ 505 PPM Cu
   0.4 N HNO3                         399 PPM Mn ↑  Heptanoic Acid
                          |    15.2 PPM Cu
                          |    11.9 PPM Mn
                          |
                          |           Water-Acid Effluent
   10 wt. %  ─────→ Stage 1 ─────→ 6050 PPM Cu
   0.4 N HNO3           ↑             5820 PPM Mn Heptanoic Acid
                             600 PPM Cu
                             600 PPM Mn
```

The data of Table II illustrate that cupric and manganous ions in heptanoic acid can be effectively extracted to less than one part per million in three extraction stages using in each stage a 10 weight percent 0.4N nitric acid as the extractant. Of the extraction procedures illustrated, a continuous counter current extraction is the preferred method.

What is claimed is:

1. A process for removing cupric and manganous metal ions from a saturated aliphatic monocarboxylic acid containing from 6 to 9 carbon atoms comprising adding to said monocarboxylic acid, water and a mineral acid whose hydrogen can be replaced by said cupric and manganous metal ions, said extractant acid being present in an amount sufficient to extract said cupric and manganous metal ions in soluble form from said monocarboxylic acid into an aqueous layer; said monocarboxylic acid collecting in a water-immiscible organic phase and said metal ions collecting in an aqueous phase, separating said organic phase from said aqeous phase and recovering said monocarboxylic acid having a substantially reduced content of said cupric and manganous metal ions.

2. The process of claim 1 wherein the amount of mineral acid is present in at least an equivalent amount per total equivalents of metals.

3. The process of claim 2 wherein the mineral acid is nitric acid.

4. The process of claim 2 wherein the mineral acid is phosphoric acid.

* * * * *